US00PP08294P

United States Patent [19]

VandenBerg

[11] Patent Number: Plant 8,294

[45] Date of Patent: Jul. 6, 1993

[54] CHRYSANTHEMUM PLANT NAMED LINDA

[75] Inventor: Cornelis P. VandenBerg, Salinas, Calif.

[73] Assignee: Yoder Brothers, Inc., Barberton, Ohio

[21] Appl. No.: 741,759

[22] Filed: Aug. 7, 1991

[51] Int. Cl.[5] ..... A01H 5/00

[52] U.S. Cl. ..... Plt./77

[58] Field of Search ..... Plt./77

[56] References Cited

U.S. PATENT DOCUMENTS

P.P. 7,517 5/1991 VandenBerg ..... Plt. 77

OTHER PUBLICATIONS

Sunnyslope Gardens. Chrysanthemums 1992. San Gabriel, Calif. p. 21.

Sunnyslope Gardens. '83 Chrysanthemums. San Gabriel Calif. p. 27.

*Primary Examiner*—Howard J. Locker

*Attorney, Agent, or Firm*—Foley & Lardner

[57] ABSTRACT

A Chrysanthemum plant named Linda particularly characterized by its flat capitulum form; decorative capitulum type; white ray floret color with light yellow center of the flower; diameter across face of capitulum of 51 to 64 mm when fully opened; branching pattern is spreading and prolific, with 7 to 9 breaks after pinch when grown outside under natural daylength in fall flowerings and in 10 cm pots for spring flowerings; natural season flower date of August 23 to 31 when planting rooted cuttings on June 21 to 23 in Salinas, Calif., and of October 2 to 5 when planting rooted cuttings June 15 to June 18 in Hightstown, N.J.; flowering response of 48 to 53 days after rooting in no light/no shade programs in spring in Salinas; plant height of 25 to 30 cm when grown in fall under natural daylength with no growth regulators in New Jersey, and of 18 to 20 cm when grown in 10 cm pots in spring with 1 to 2 applications of 2500 ppm B-9 SP; and durable, uniform performance.

3 Drawing Sheets

The present invention comprises a new and distinct cultivar of Chrysanthemum, botanically known as *Dendranthema grandiflora,* and referred to by the cultivar name Linda.

Linda, identified as 8481 (86-490001), was originated from a cross made by Cornelis P. VandenBerg in a controlled breeding program in Salinas, Calif., in 1985.

The female parent of Linda was the unnamed seedling, identified at 2625 (82-M49004), and described as a white decorative garden mum; flower diameter of 64 to 76 mm; natural season flower date of August 24 to 27 in Salinas, Calif., and of September 26 to 30 in Hightstown, N.J.; a flowering response in spring of 48 to 54 days; plant height of 25 to 28 cm in fall natural season flowerings in New Jersey, and of 20 to 23 cm in spring flowerings in 10 cm pots with no growth regulator in Salinas. The female parent of Linda was discarded from the program in October 1987.

The male parent of Linda as also an unnamed seedling, identified as 0313 (83-645001) and described as a white daisy garden mum; flower diameter of 32 mm; natural season flower date of August 24 to 28 in Salinas, Calif., and of September 28 to 29 in Hightstown, N.J.; a flowering response in spring of 51 to 52 days; plant height of 33 cm in fall natural season flowering in New Jersey, and of 20 to 25 cm in spring flowerings in 10 cm pots with no growth regulator in Salinas. The male parent of Linda was discarded from the program in May 1988.

Linda was discovered and selected as one flowering plant within the progeny of the stated cross by Cornelis P. VandenBerg in September 1986, in a controlled environment in Salinas, Calif.

The first act of asexual reproduction of Linda was accomplished when vegetative cuttings were taken from the initial selection in November 1986 in a controlled environment in Salinas, Calif., by technicians working under supervision of Cornelis P. VandenBerg.

Horticultural examination of controlled flowerings of successive plantings has shown that the unique combination of characteristics as herein disclosed for Linda are firmly fixed and are retained through successive generations of asexual reproduction.

Linda has not been observed under all possible environmental conditions. The phenotype may vary somewhat with variations in environment such as temperature, light intensity and daylength, without, however, any variance in the genotype.

The following observations, measurements and comparisons described plants grown in Salinas, Calif., and in Hightstown, N.J. Rooted cuttings were established in soil and maintained outdoors under the natural temperature and daylength prevailing during June through October. Spring flowerings were conducted in Salinas, Calif. under greenhouse conditions which approximate those generally used in commercial greenhouse practice for small pot spring garden mum production.

The following traits have been repeatedly observed and are determined to be basic characteristics of Linda, which, in combination, distinguish this Chrysanthemum as a new and distinct cultivar:

1. Flat capitulum form.
2. Decorative capitulum type.
3. White ray floret color with light yellow center of the flower.
4. Diameter across face of capitulum of 5 1 to 64 mm when fully opened.
5. Branching pattern is spreading and prolific, with 7 to 9 breaks after pinch when grown outside under natural daylength in fall flowerings and in 10 cm pots for spring flowerings.

6. Natural season flower date of August 23 to 31 when planting rooted cuttings on June 21 to 23 in Salinas, Calif., and of October 2 to 5 when planting rooted cutitngs June 15 to 18 in Hightstown, N.J.

7. Flowering response of 48 to 53 days after rooting in no light/no shade programs in spring in Salinas.

8. Plant height of 25 to 30 cm when grown in fall under natural daylength with no growth regulators in New Jersey, and of 18 to 20 cm when grown in 10 cm in spring with 1 to 2 applications of 2500 ppm B-9 SP.

9. Durable, uniform performance.

The accompanying photographic drawings show typical inflorescence and leaf characterisatics of Linda, with the colors being as nearly true as possible with illustrations of this type.

Sheet 1 is a color photograph of Linda grown as a pinched spray pot mum with 1 cutting in a 10 cm pot.

Sheet 2 is a black and white photograph of three views of the inflorescence of Linda.

Sheet 3 is a black and white photograph showing the upper and under sides of the leaves of Linda at 3 stages of development (mature, intermediate and immature). In sheets 2 and 3 a measuring tape in centimeters has been added.

Of the commercial cultivars known to the inventor, the most similar in comparison to Linda is the cultivar identified as Nicole, disclosed in U.S. Plant Pat. No. 7,517. Reference is made to attached Chart A, which compares certain characteristics of Linda to the same characteristics of Nicole, when both cultivars are grown side by side under the same growing conditions.

Similar traits are ray floret color, capitulum form and type and branching pattern. Diameter of capitulum, natural season flower date in Salinas fall flowerings, controlled response and plant height of Linda and Nicole fall into the same range. Natural season flower date in New Jersey of Linda is signficantly later than the flowering date of Nicole under the same conditions. This is an important trait, and Linda was specifically selected for this trait in order to extend the natural season flowering period for white decorative garden mums by more than one week.

In the following description color references are made to the Royal Horitcultural Society Colour Chart. The color values were determined on plant material grown as a pinched spray pot mum in a 10 cm pot in Salinas, Calif. on Apr. 15, 1991.

Classification:

*Biotanical.*—*Dendranthema grandiflora* cv. Linda.

*Commercial.*—Flat decorative spray pot mum and garden mum.

IINFLORESCENCE

A. Capitulum:

*Form.*—Flat.

*Type.*—Decorative.

*Diameter across face.*—51 to 64 mm when fully opened.

B. Corolla of ray florets:

*Color (general tonality from a distance of three meters).*—White, with light yellow center of flower.

*Color (upper surface).*—155D, with center of flower closest to 2D to 4D.

*Color (under surface).*—155D.

*Shape.*—Cross section concave, longitudinal section of outer ray florets convex.

C. Corolla of disc florets:

*Color (mature).*—14B.

*Color (immature).*—144C.

D. Reproductive organs:

*Androecium.*—Present on disc florets only, no to very scant pollen.

*Gynoecium.*—Present on both ray and disc florets.

PLANT

A. General appearence:

*Height.*—25 to 30 cm when grown in fall under natural daylength in New Jersey with no growth regulators, and of 18 to 20 cm when grown in 10 cm pots in spring in Salinas with 1 to 2 applications of 2500 ppm B-9 SP.

*Branching pattern.*—Spreading and prolific, with 7 to 9 breaks after pinch when grown outside under natural daylength in fall flowerings and in 10 cm pots for spring flowerings.

B. Foliage:

*Color (upper surface).*—147A.

*Color (under surface).*—147B.

*Shape.*—See photograph.

CHART A

| CULTIVAR | LINDA | NICOLE |
|---|---|---|
| Ray floret color | White with light yellow center | White with light yellow center |
| Capitulum form and type | Flat decorative | Flat decorative |
| Diameter across face of capitulum | 51 to 64 mm | 44 to 63 mm |
| Branching pattern | Spreading and prolific | Spreading and prolific |
| Natural season flower date: | | |
| in Salinas, CA | Aug. 23 to 31 | Aug. 17 to 26 |
| in Hightstown | Oct. 2 to 5 | Sept. 17 to 27 |
| Controlled response | 48 to 53 days | 45 to 54 days |
| Plant height: | | |
| in natural season fall | 25 to 30 cm | 23 to 30 cm |
| in 10 cm pots spring | 18 to 20 cm | 18 to 23 cm |

COMPARISONS MADE OF PLANTS GROWN AS UNDER NATURAL SEASON OUTDOOR CONDITIONS IN SALINAS, CALIFORNIA AND IN HIGHTSTOWN, NEW JERSEY AND IN SPRING FLOWERING PROGRAMS IN SALINAS, CALIFORNIA

I claim:

1. A new and distinct Chrysanthemum plant named Linda, as described and illustrated.

* * * * *

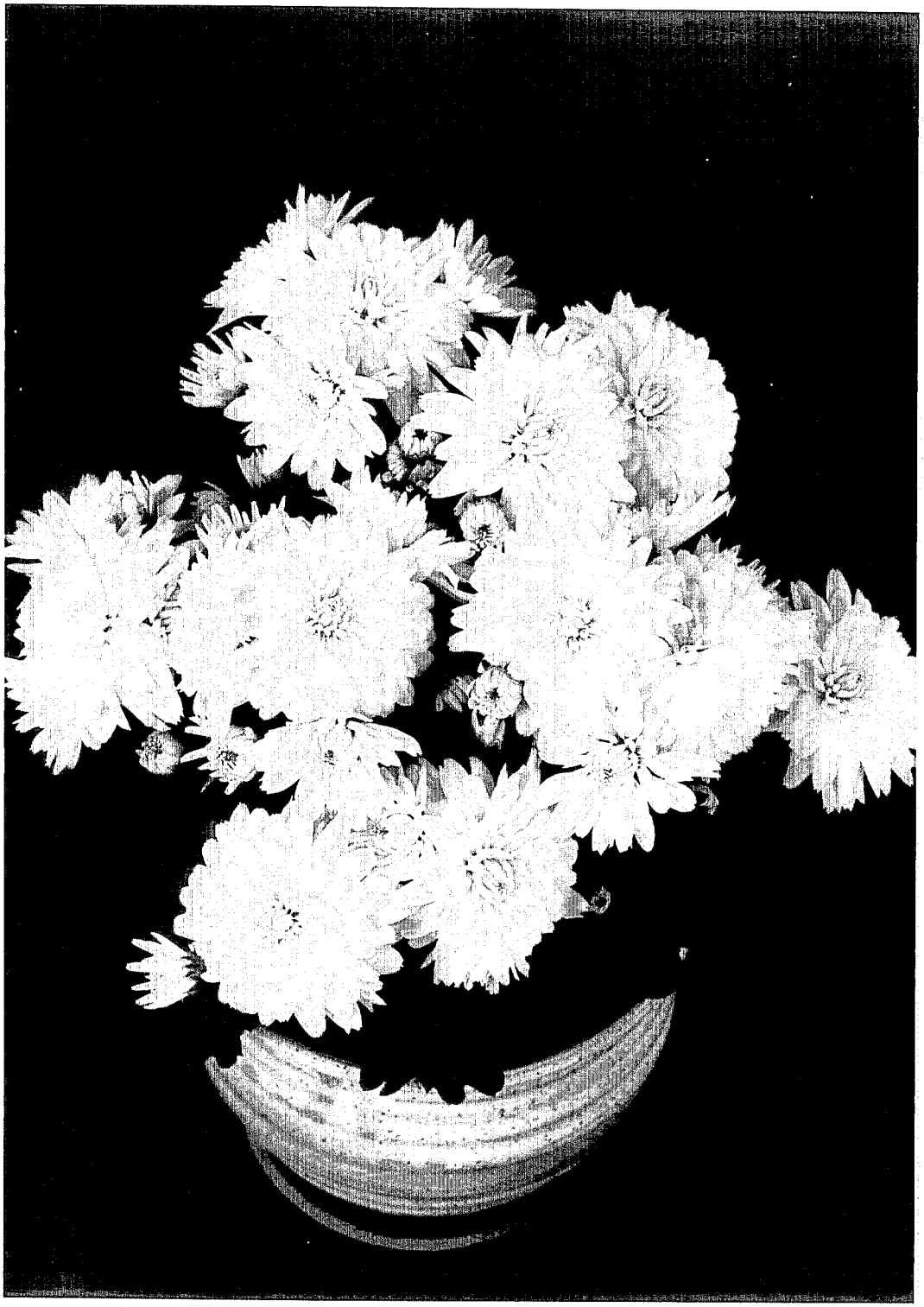

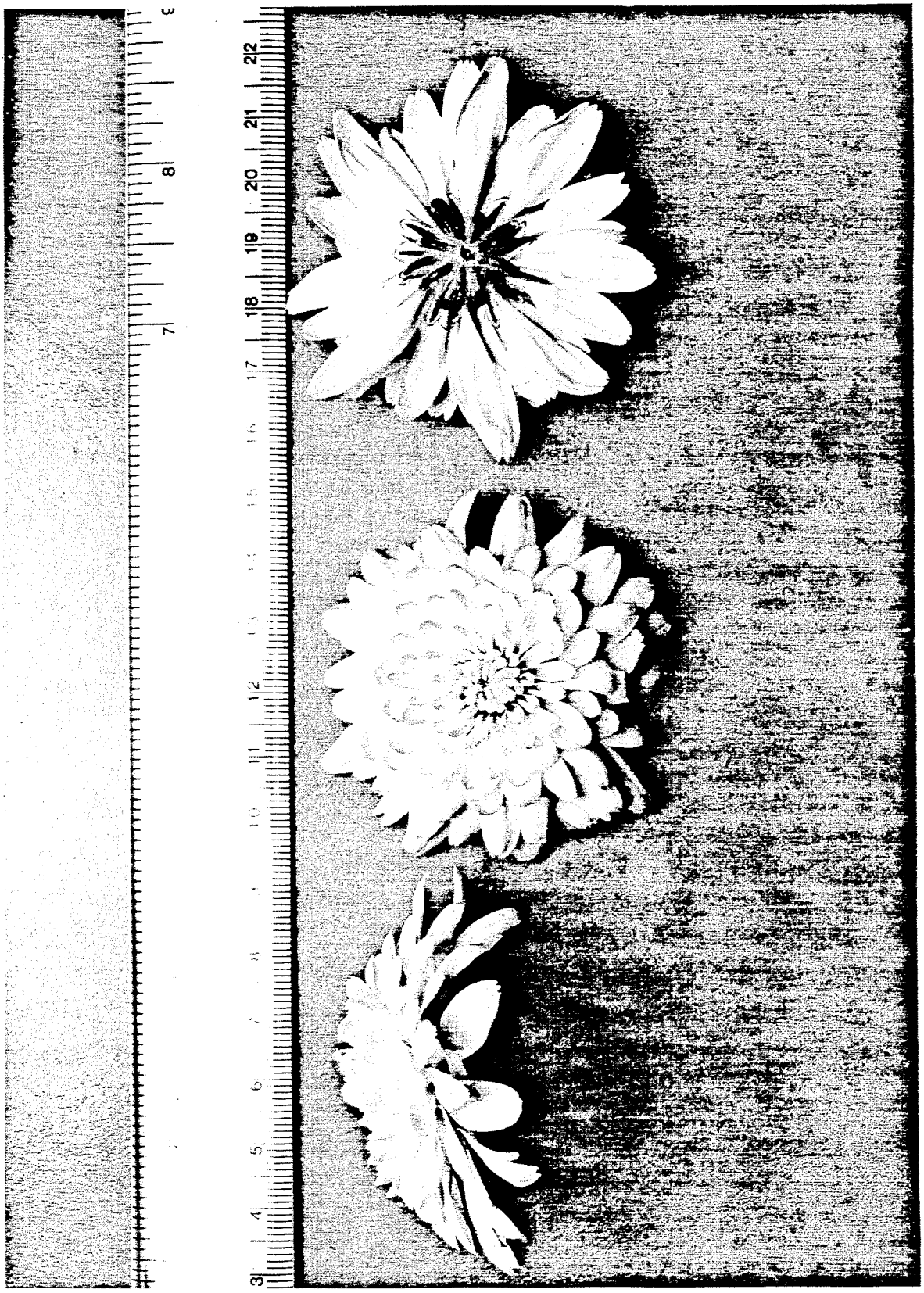

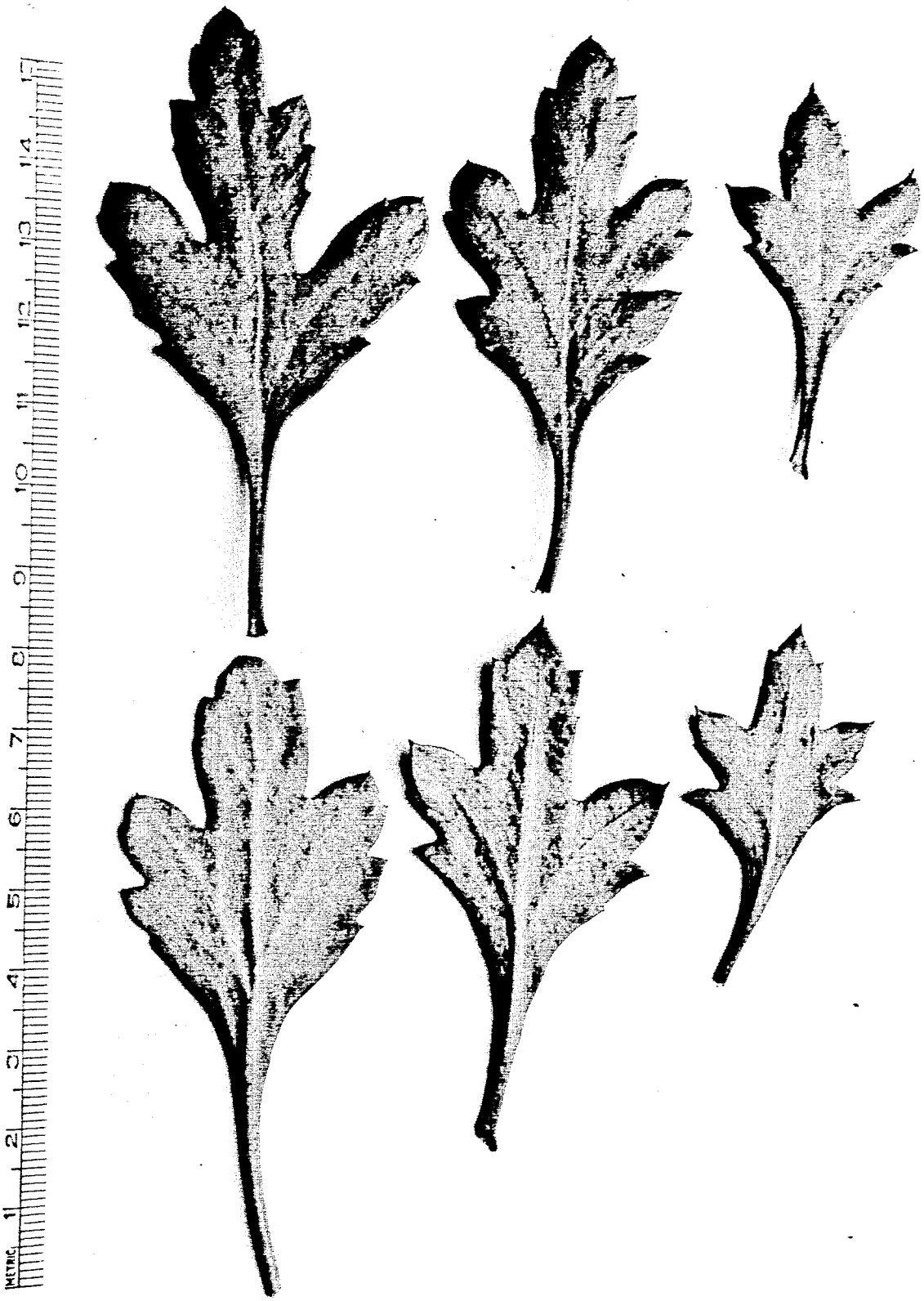
METRIC
1
2
3
4
5
6
7
8
9
10
11
12
13
14
15